(12) United States Patent
Buszman et al.

(10) Patent No.: US 12,102,527 B2
(45) Date of Patent: Oct. 1, 2024

(54) BIOLOGICAL LOW PROFILE, BALLOON EXPANDABLE PROSTHETIC HEART VALVE, PARTICULARLY AORTIC, FOR TRANSCATHETER IMPLANTATION AND THE METHOD OF ITS MANUFACTURING

(71) Applicants: AMERICAN HEART OF POLAND S.A., Ustroń (PL); CENTRUM MATERIAŁÓW POLIMEROWYCH I WĘGLOWYCH POLSKIEJ AKADEMII NAUK, Zabrze (PL); POLITECHNIKA ŚLĄSKA WYDZIAŁ MECHANICZNY TECHNOLOGICZNY, Gliwice (PL); ŚLĄSKIE CENTRUM CHORÓB SERCA W ZABRZU, Zabrze (PL); ZAKŁAD DOŚWIADCZALNY INSTYTUTU ZOOTECHNIKI PIB GRODZIEC ŚLĄSKI SP. Z O.O., Świętoszówka (PL); INNOVATIONS FOR HEART AND VESSELS SP. Z O.O., Tychy (PL); HEART TEAM SP. Z O.O., Warsaw (PL)

(72) Inventors: Pawel Buszman, Katowice (PL); Mariusz Pawlak, Zabrze (PL); Wojciech Klein, Knurow (PL); Jacek Gnilka, Gliwice (PL); Arkadiusz Mezyk, Gliwice (PL); Marian Zembala, Tarnowskie Gory (PL); Joanna Sliwka, Zabrze (PL); Marzena Bialek-Brodocz, Bielsko-Biala (PL); Krzysztof Milewski, Katowice (PL); Piotr Buszman, Katowice (PL); Piotr Hirnle, Warsaw (PL); Jerzy Nozynski, Zabrze (PL); Michal Zembala, Zabrze (PL)

(73) Assignee: INNOVATIONS FOR HEART AND VESSELS SP. Z O.O., Katowice (PL)

(*) Notice: Subject to any disclaimer, the term of this patent is extended or adjusted under 35 U.S.C. 154(b) by 780 days.

(21) Appl. No.: 17/262,430

(22) PCT Filed: Jul. 26, 2018

(86) PCT No.: PCT/PL2018/050037
§ 371 (c)(1),
(2) Date: Jan. 22, 2021

(87) PCT Pub. No.: WO2020/022913
PCT Pub. Date: Jan. 30, 2020

(65) Prior Publication Data
US 2021/0290377 A1    Sep. 23, 2021
US 2022/0104939 A2    Apr. 7, 2022

(30) Foreign Application Priority Data

Jul. 24, 2018  (PL) .......................... 426429

(51) Int. Cl.
*A61F 2/24* (2006.01)

(52) U.S. Cl.
CPC .......... *A61F 2/2409* (2013.01); *A61F 2/2433* (2013.01); *A61F 2220/0075* (2013.01); *A61F 2240/001* (2013.01)

(58) Field of Classification Search
CPC ............ A61F 2/2409; A61F 2220/0075; A61F 2/2412
See application file for complete search history.

(56) References Cited

U.S. PATENT DOCUMENTS 4,477,930 A * 10/1984  Totten ................... A61F 2/2409
                                                        623/2.15
4,759,758 A *  7/1988  Gabbay ................. A61F 2/2412
                                                        623/2.13

(Continued)

FOREIGN PATENT DOCUMENTS

EP     2399550 A1 * 12/2011  ........... A61F 2/2409
EP     1637176 B1    6/2016

(Continued)

OTHER PUBLICATIONS

Visegrad Patent Institute, International Search Report for Application PCT/PL2018/050037, dated Jan. 11, 2019.

(Continued)

*Primary Examiner* — Suzette J Gherbi

(74) *Attorney, Agent, or Firm* — Cherskov Flaynik & Gurda, LLC

(57) ABSTRACT

A biological low profile balloon expandable prosthetic heart valve, particularly aortic for transcatheter implantation comprising a valve frame of cylindrical design which consists of a valve section, a supporting section and a biological material sewn thereto. The upper part of the cylindrical cuff made of the biological material is attached to the valve frame in the supporting section on the outside and the cuff is folded to the interior of the frame and it is attached to the posts in the valve section. The upper parts of the cuff which are not attached to the posts, on each side of the post are connected with each other on the valve frame establishing commissures for the valve leaflets.

5 Claims, 3 Drawing Sheets

(56) References Cited

U.S. PATENT DOCUMENTS

Figure 1:
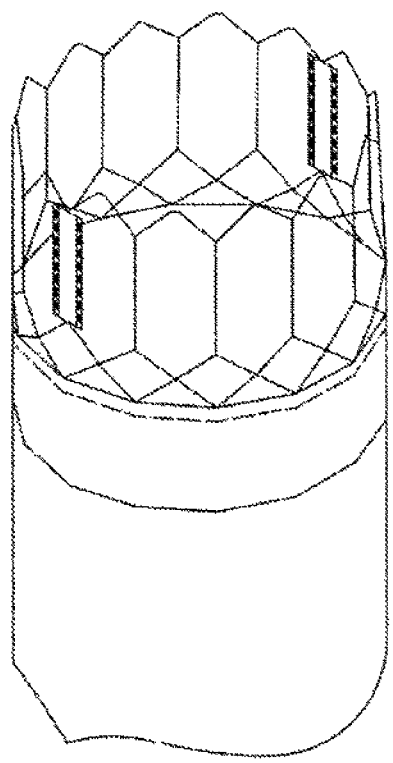

| | | | |
|---|---|---|---|
| 5,549,635 A | 8/1996 | Solar | |
| 5,984,973 A | 11/1999 | Girard et al. | |
| 6,007,543 A | 12/1999 | Ellis et al. | |
| 6,010,529 A * | 1/2000 | Herweck | C08L 27/18 |
| | | | 623/23.69 |
| 11,517,428 B2 * | 12/2022 | Shang | A61F 2/2436 |
| 2003/0171805 A1 * | 9/2003 | Berg | A61F 2/2418 |
| | | | 623/2.14 |
| 2005/0113910 A1 * | 5/2005 | Paniagua | A61F 2/2412 |
| | | | 623/2.14 |
| 2005/0240262 A1 * | 10/2005 | White | A61F 2/2415 |
| | | | 623/901 |
| 2011/0098802 A1 * | 4/2011 | Braido | A61F 2/2412 |
| | | | 623/2.11 |
| 2012/0078353 A1 * | 3/2012 | Quadri | A61F 2/2436 |
| | | | 623/2.14 |
| 2012/0078356 A1 * | 3/2012 | Fish | A61F 2/2418 |
| | | | 29/890.12 |
| 2012/0185038 A1 * | 7/2012 | Fish | A61F 2/2415 |
| | | | 493/405 |
| 2014/0135911 A1 * | 5/2014 | Spenser | A61F 2/9524 |
| | | | 623/2.19 |
| 2017/0014229 A1 | 1/2017 | Nguyen-Thien-Nhon et al. | |
| 2018/0185143 A1 * | 7/2018 | Fish | A61F 2/2415 |
| 2023/0147439 A1 * | 5/2023 | Shang | A61L 27/3633 |
| | | | 623/2.11 |
| 2023/0218390 A1 * | 7/2023 | Pisani | A61F 2/2418 |
| | | | 623/2.18 |
| 2023/0255756 A1 * | 8/2023 | Corona | A61M 25/10 |
| | | | 623/2.18 |

FOREIGN PATENT DOCUMENTS

| | | |
|---|---|---|
| WO | WO2018004871 A1 | 1/2018 |
| WO | WO2018011592 A1 | 1/2018 |
| WO | WO-2018093711 A3 * | 7/2018 ........... A61F 2/2412 |

OTHER PUBLICATIONS

Mateusz Kachel et al., State-of-the-art of Transcatheter Treatment of Aortic Valve Stenosis and the Overview of the InFlow Project Aiming at Developing the first Polish TAVI System, Cardiology Journal 2017, pp. 685-694, vol. 24, No. 6. Published Dec. 29, 2017 in Poland.

Saskia Julich, European Search Report in Application EP 18 92 7966, completed on Mar. 30, 2022.

* cited by examiner cuff sewn

BIOLOGICAL LOW PROFILE, BALLOON EXPANDABLE PROSTHETIC HEART VALVE, PARTICULARLY AORTIC, FOR TRANSCATHETER IMPLANTATION AND THE METHOD OF ITS MANUFACTURING

The present invention relates to a biological low profile, balloon expandable prosthetic aortic valve for transcatheter implantation and the method of its manufacturing. The invention relates to medical devices and developments used in treatment of cardiovascular system valve defects.

Use of this type of device involves its manufacturing and implantation by minimally invasive percutaneous method in the place of a native valve which is impaired due to a congenital or acquired defect. Implantation is carried out under fluoroscopy by means of a low profile delivery system. This procedure is a recommended method of treating valvular disfunctions in a chosen group of patients with left arterial outflow tract stenosis, allowing to restore its functionality.

Aortic stenosis (AS) which is left arterial outflow tract obstruction is nowadays the most frequently occurring valve defect posing a serious clinical challenge for doctors. The reason is the growing number of elderly patients who cannot undergo a standard cardiac surgery due to surgical risks. It is estimated that with age the prevalence of aortic stenosis rises from 0,7% in patients 18-44 years old up to 13,3% in patients after >75 years old (publications: Nkomo V. T., Gardin J. M., Skelton T. N., et al., Burden of valvular heart disease: a population-based study. *Lancet*, 2006. 368(9540): p. 1005-11 DOI: 10.1016/50140-6736(06)69208-8). European Society of Cardiology (ESC) in the recommendations from 2012 estimates that 2-7% Europeans and Americans over 65 years of age suffer from this condition. (Joint Task Force on the Management of Valvular Heart Disease of the European Society of C., European Association for Cardio-Thoracic Surgery, Vahanian A., et al., Guidelines on the management of valvular heart disease (version 2012). *Eur Heart J*, 2012. 33(19): p. 2451-96 DOI: 10.1093/eurheartj/ehs109). In the event that concomitant symptoms appear with impaired blood flow surgical treatment is indispensible, since without it the prognosis worsens significantly. Currently the basic method of treatment (gold standard) is the surgical aortic valve replacement (SAVR) which comprises implantation of a biological or mechanical prosthesis. However, this procedure affects major organs, especially in case of elderly patients (>70 years of age) among whom perioperational mortality rises with age from 1-3% to 4-8%, which is quoted in Guidelines on the management of valvular heart disease. It translates into a high percentage of patients disqualified from surgical treatment (⅓ of patients>75 years of age). It particularly refers to patients with concomitant afflictions of other organs and with high surgical risk (Euroscore 2>10%)(lung B., Cachier A., Baron G., et al., *Decision-making in elderly patients with severe aortic stenosis: Why are so many denied surgery? Eur Heart J*, 2005. 26(24): p. 2714-20 DOI: 10.1093/eurheart/ehi471). The alternative for such patients is a minimally-invasive method introduced into clinical setting in 2002, so-called Transcatether Aortic Valve Replacement (TAVR). The efficacy of this method compared to conventional (surgical) method has been confirmed by the outcomes of numerous completed and ongoing trials in both high risk and lower risk patients (publications:Mack M. J., Leon M. B., Smith C. R., et al. 5-year outcomes of transcatheter aortic valve replacement or surgical aortic valve replacement for high surgical risk patients with aortic stenosis (PARTNER 1): a randomized controlled trial. *The Lancet*, 2015. 385(9986): p. 2477-2484 DOI: 10.1016/s0140-6736(15)60308-7; Deeb G. M., Reardon M. J., Chetcuti S., et al., 3-Year Outcomes in High-Risk Patients Who Underwent Surgical or Transcatheter Aortic Valve Replacement. *J Am Coll Cardiol*, 2016.67(22): p. 2565-74 DOI: 10.1016/j.jacc.2016.03.506; Leon M. B., Smith C. R., Mack M. J., et al., Transcatheter or Surgical Aortic-Valve Replacement in Intermediate-Risk Patients. *N Engl J Med*, 2016. 374(17): p. 1609-20 DOI: 10.1056/NEJMoa1514616; Sondergaard L, Steinbruchel D. A., Ihlemann N., et al., Two-Year Outcomes in Patients With Severe Aortic Valve Stenosis Randomized to Transcatheter Versus Surgical Aortic Valve Replacement: The All-Comers Nordic Aortic Valve Intervention Randomized Clinical Trial. *Circ Cardiovasc Interv*, 2016. 9(6) DOI: 10.1161/CIRCINTERVENTIONS.115.003665)-7)

Despite undisputed benefits, TAVR is not free from significant constraints. Relatively frequently occurring vascular injuries (4.13%) are caused mainly by large delivery systems, which although much smaller than the ones used originally (average drop from 24 F to 18 F), still need miniaturization (da Gama Ribeiro V., Vouga L., Markowitz A., et al., Vascular access in transcatheter aortic valve implantation. *Int J Cardiovasc Imaging*, 2011.27(8): p. 1235-43 DOI: 10.1007/s10554-011-9900-8; Cribier A., The Odyssey of TAVRfrom Concept to Clinical Reality. Tex Heart Inst J, 2014. 41(2) DOI: 10.14503/THIJ-14-4137; Halapas A., Chrissoheris M., Bouboulis N., et al., Update on current TAVI 3 technology, indications, screening, and outcomes. Continuing Cardiology Education, 2016. 2(1): p. 37-46 DOI: 10.1002/cce2.20).

Another essential issue is the higher frequency of paravalvular leakage (PVL) occurring in patients after TVR procedure in comparison to patients after a classical surgical procedure. The complex valve anatomy and imperfect expandable systems cause the risk of uneven opening of the prosthetic heart valve as well as its Impaired apposition to the native annulus and bulb. Connected with the above mentioned issue inability to subsequent implantation of a prosthesis and its movement in case of malpositioning poses a serious challenge for scientists and constructors. These problems are addressed in detail in the publication Mollmann H., Kim W. K., Kempfert J., et al., Complications of transcatheter aortic valve Implantation (TAVI): how to avoid and treat them. *Heart*, 2015. 101(11): p. 900-8 DOI: 10.1136/heartjnl-2013-304708.

Applying biological materials for manufacturing currently used TAVI prostheses rises the problem of durability. The implant like any other tissue degenerates with time and is subject to processes such as calcification or vegetation. It is essential to find methods which can improve durability and immunity of currently used materials preserving their flexibility and biocompatibility. There is another significant aspect influencing spreading of TAVR method in the world that should be noted, namely its price. Wealthy countries such as Germany and Switzerland are able to cover costs of only 34,5% and 36,2% of the demand for the therapy respectively while the European average is around 17,9%. The ideal prosthetic heart valve should be made of durable materials resistant to degradation, with biophysical properties to the greatest extent similar to native leaflets or of natural materials modified properly so that their mechanical parameters are reinforced and improved.

The prosthetic heart valve known from the patent description WO2018011592 has leaflets made of a biological material sewn into a frame, a sewing ring. The ring comprises elements for attaching the leaflets with a suture or other attaching materials. However, this construction does not allow perfect stabilization of the whole valve construction as well as for its appropriate and stable apposition to vascular walls. Additionally, this method does not allow to form the valve leaflets without cutting and preliminary forming the material in order to form the leaflet structures, which can cause impaired apposition and closing (coaptation) of the leaflets and as a result leakage and defective closure. This way of fabricating is time-consuming. What is more, intrusion into the structure of the leaflet material may cause its damage, which contributes to formation of leakages or coagulation on the material edges undergoing treatment.

The prosthetic heart valve known from the patent description WO2018004871 comprises a metal stent with longitudinal and transverse meshes. The construction resembling commercially available valves of metal frame connected with bovine or porcine pericardium which undergoes various processes of chemical and biological modification with sowing stem cells. The above mentioned modification methods improve the quality of a biological material and decrease the risk of calcification and coagulation. These methods do not affect the quality of valve activity, hence ruling out the risk of improper leaflet motion and in consequence defective closure of the valve. However, introducing so many modifications significantly rises the costs of fabricating and increases the time of production.

The prosthetic heart valve known from the patent description U.S. Pat. No. 5,984,973 is made of a natural material, it consists of a metal frame to which a biological material forming the leaflets is sewn by a continuous suture line with a monofilament suture. In the upper part of the frame there are 3 vertical posts evenly located in relation to the diameter of the frame, on which the biological material is wound and sewn by circular suture line creating commissures which form the leaflets. Continuous sewing with a single commissure suture is less resistant to mechanical damage and destruction. Damage in any place of such mounting may cause untwisting of the commissure, stripping of the material and damage of the valve. Additionally, pulling the material onto vertical posts located in the upper part of the valve frame may cause damage and ripping of the delicate biological material used for forming leaflets due to valve activity and mechanical overload.

The aim of the invention is to eliminate the defects of the existing prosthetic heart valves as well as to reduce the cost of manufacturing by use of an improved (optimized) method of manufacturing the valve leaflets and a manner of sewing them.

The invention refers to a biological low profile balloon expandable prosthetic heart valve, particularly aortic, for transcatheter implantation, comprising a cylindrical valve frame which consists of a valve section, supporting section and a biological material sewn thereto. The upper part of a cylindrical cuff made of a biological material is attached to the valve frame in its supporting section on the outside and the cuff is folded to the interior of the frame from below and it is attached to the attaching posts in the valve section, and the upper parts of the cuff which are not fastened to the supporting posts, on each side of the post, are connected with each other on the valve frame establishing commissures for the valve leaflets. Attaching the biological cuff to the valve frame and to the posts for attaching the cuff in the valve section is done by sewing, favourably with use of a surgical suture. Sewing commissures in the frame area and in the area of the post for attaching the cuff is made with a monofilament suture, whose both ends alternately conducted through the adjacent edges of the created valve leaflets move towards the frame, and on the first suture line between the valve leaflets there is a protrusion made on the suture, favourably in the form of a knot.

The invention also refers to a method of manufacturing a biological low profile, balloon expandable prosthetic aortic valve for transcatheter implantation comprising the cylindrical valve frame which consists of a valve section, supporting section and a biological material sewn thereto. The upper part of a cylindrical cuff made of a biological material is attached to the valve frame in its supporting section on the outside, and the lower unattached part of the cuff is folded and it is inserted to the interior of the frame from below and it is attached to the attaching posts in the valve section, and the upper parts of the cuff which are not attached to the supporting posts, on each side of the post, are connected with each other on the valve frame establishing commissures for the valve leaflets. Sewing commissures in the frame area and in the area of the post for attaching the cuff is made with a monofilament suture, whose both ends alternately conducted through the adjacent created valve leaflets move towards the frame for the distance of 2 mm. On the first suture line between the valve leaflets there is a protrusion made on the suture, favourably in the form of a knot.

The prosthetic heart valve of the present invention is characterised by high biocompatibility and of a low profile, which enables applying the delivery system of the smallest diameter possible. It adheres well to the aortic annulus in the supporting section for eliminating the risk of leakages. It is possible to reposition the valve with use of a special implantation system including a balloon of a "dog bone" type.

The method of forming the prosthetic heart valve and its leaflets takes less time than currently used methods of fabricating biological prosthetic heart valves, which is approximately 3 hours. So far the whole process has taken a few days. Furthermore, applying the method of forming the cylinder folded into the interior of the valve frame for forming its leaflets by creating commissures, allows to eliminate the need to form them from a number of separate elements, thanks to which the whole construction and the material are more durable and resistant to damage and tear. This method also allows to eliminate a big number of places of sewing which are most prone to be damaged. Moreover, use of alternate interlacing of sutures in the place of commissure allows to avoid tearing of the whole mounting in the event of one thread being torn and the whole bicuspid or tricuspid structure is still preserved—a commissure is still supported by the other part of the suture. Additionally, the unique manner of sewing allows to create pockets between a frame and a valve leaflet, which further improves apposition of leaflets to each other (coaptation) and they prevent the leakage as well as allow free blood circulation as they do not cause build-up of blood between the valve leaflet material and the frame. Additionally, direct apposition of the cuff to the valve frame lowers the risk of occurrence of free space, by means of which paravalvular leakages are eliminated.

Adopting the above mentioned solutions significantly reduces the time of valve fabricating, which in turn should relevantly lower the costs of production and increase competitiveness of the product. It should translate into the widest possible use and further development of minimally invasive methods of repairing the aortic valve and other valves.

Figure 2:
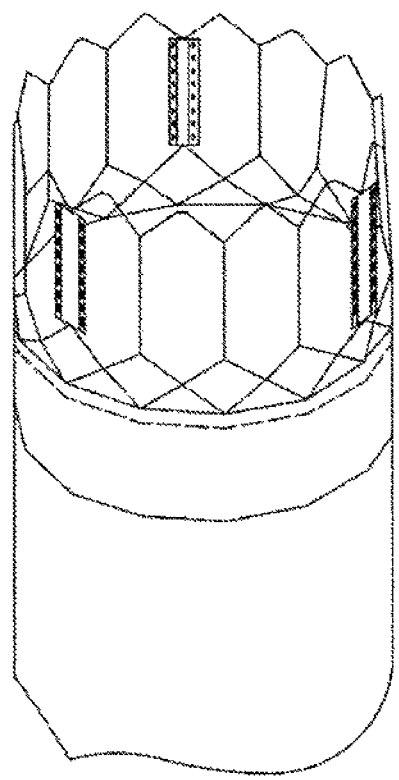
Figure 3:
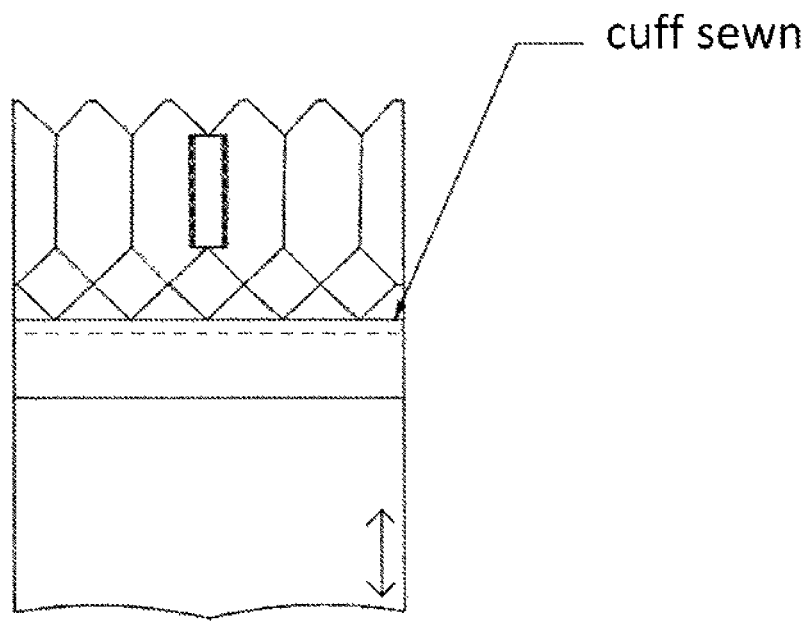
Figure 4:
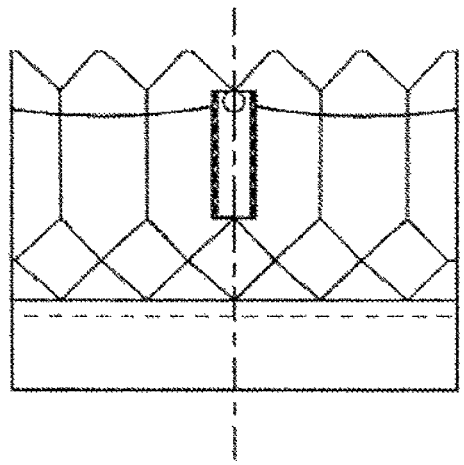
Figure 5:
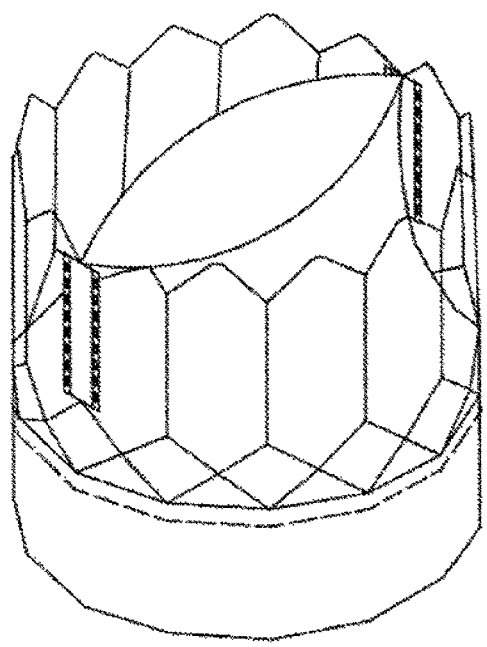
Figure 6:
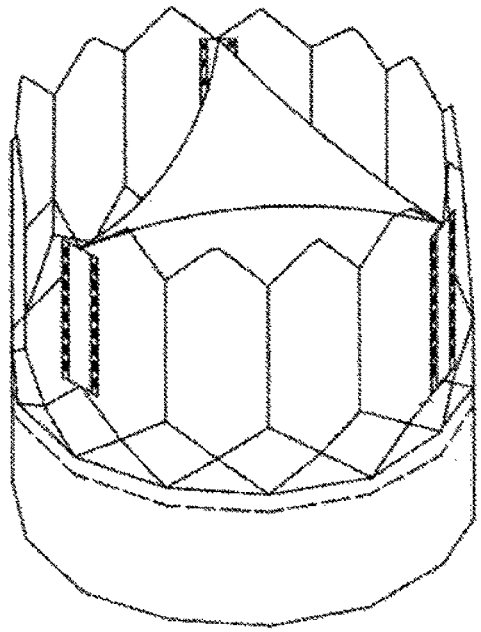
Figure 7:
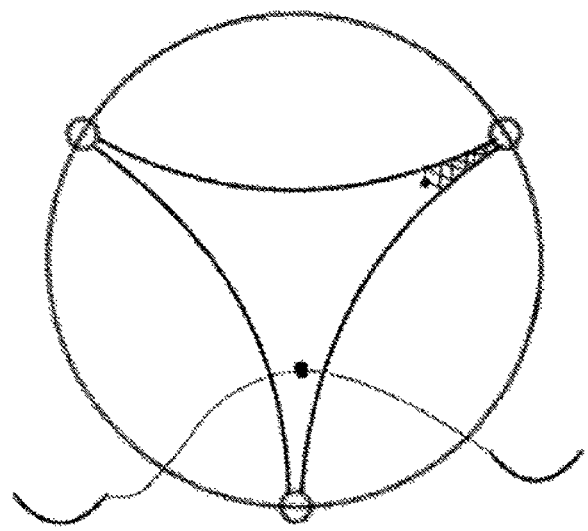
Figure 8:
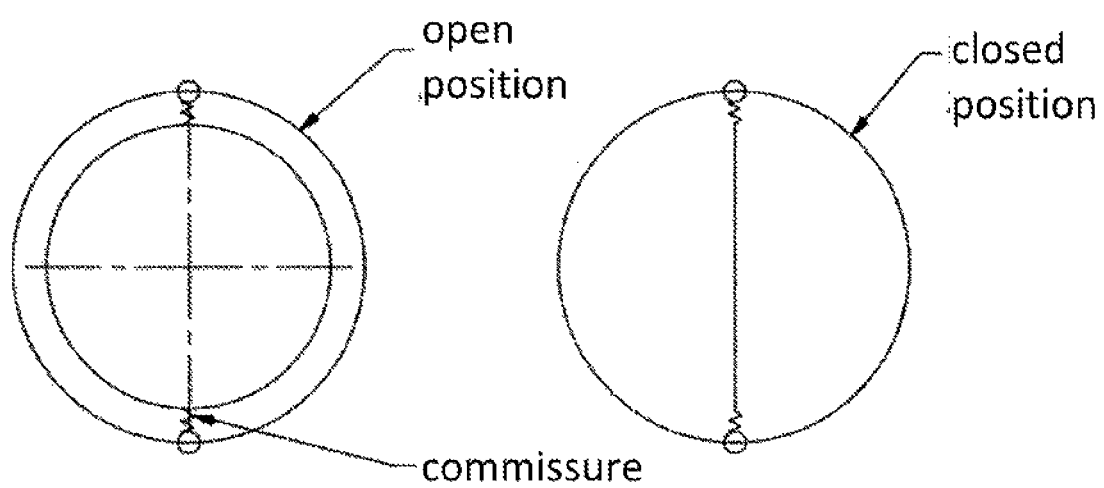
Figure 9:
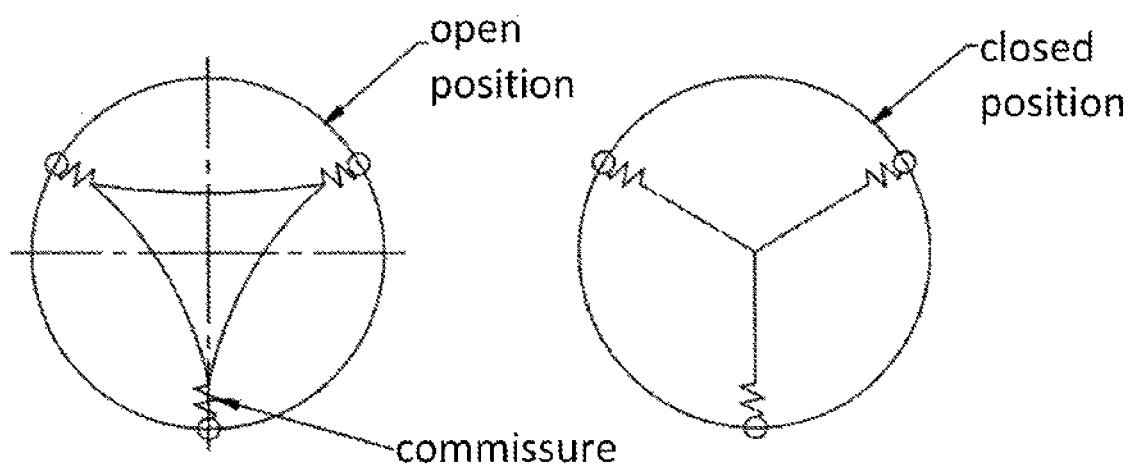

The Invention is presented in the examples of realization in the drawings, in which FIG. 1 shows the stent shoulder of the bicuspid heart valve with the biological material sewn thereto and formed in the shape of a cylinder, FIG. 2 shows the stent shoulder of the tricuspid valve with the biological material sewn thereto and formed in the shape of a cylinder, FIG. 3 shows the projection view from the front of the valve stent with the biological material sewn thereto and with the marked place of mounting in the valve section of the valve frame, FIG. 4 shows the projection view from the front of the valve stent with the biological material folded inwards with the marked place of mounting in the valve section of the valve frame, FIG. 5 shows a bicuspid valve formed by folding the biological material previously sewn into and formed into the shape of a cylinder into the interior of the frame and by sewing the commissures, FIG. 6 shows a tricuspid valve formed by folding the biological material previously sewn into, formed into the shape of a cylinder into the interior of the frame and by sewing the commissures, FIG. 7 shows the manner of creating commissures, FIG. 8 shows the commissures in a bicuspid valve in the closed and open position and FIG. 9 shows the commissures in a tricuspid valve in the closed and open position.

Shown below is an innovative model of the biological valve, particularly aortic, intended for treatment of cardiovascular system valve defects with the use of minimally invasive method.

The aortic valve comprises a metal stent of a cylindrical design covered by a cuff made of a biological material (modified pericardium). The method used for forming the cuff and for attaching the biological material to the frame finally gives the basis to form a biological aortic valve either bicuspid or tricuspid.

The metal frame of the valve sized 16-29 mm of a cylindrical design with the possibility for radial expansion comprising two parts:

The lower part (supporting) made of the posts 0.4 mm thick which are connected with each other in the manner ensuring durability and enabling sewing the modified biological material onto the valve frame. The posts of the supporting section are connected with each other in a right-handed or left-handed design. The size of the basal meshes of the supporting section is in the range of 4-5 mm while the meshes of the middle section and the section connected with the valve frame are sized 3-4 mm.

The upper part (valve) consists of the posts located parallel to the axe of the supporting frame. The valve frame is made of two kinds of basal posts and the posts onto which the material is attached in order to form the valve leaflets.

The first (lower) ends of the valve frame posts are connected with the supporting frame struts while the others (upper) being connected to each other create the upper border of the valve.

The height of the valve frame mesh (in the direction parallel to the frame axe) is between 17 and 18 mm, branching off they connect with the adjacent struts of the valve frame also in a right-handed or left-handed design.

The design of the valve frame ensures fixed length of the frame in the process of compression and expansion. Additionally, it allows obtaining a low profile and coherent structure similar to a tube after tightening the stent.

Thanks to the post thickness change in the lower part and thanks to application of appropriate parameters the effect of "dog bone" is obtained in the scaffolding. The frame design ensures low traumatization of tissues during implantation and thanks to high radial strength enables obtaining optimal hemodynamic parameters.

The biological material in the form of sheets of porcine pericardium from which the valve leaflets are formed is widely used in the valves admitted to trading on a regulated market. The sheets are obtained from breeding pigs kept on a special diet, which allows their proper growth. Thereafter pericardium is purified and carefully selected by a qualified staff so as to choose the best quality some (taking into consideration flexibility, smoothness of the texture and cohesion). The material is cut in the shape of a square with a side length of the range 8-11 cm. Afterwards two opposite sides are connected to each other creating a cylinder (cuff) which is placed onto the supporting section of the valve frame from the outside and it is sewn thereto by a continuous suture line either single or double. The other part of the cuff is folded into the interior of the stent. The surplus of the material which stands out in the frame valve section is used to create commissures which properly made constitute the valve leaflets either bicuspid or tricuspid. The edges of the valve leaflets are attached along the vertical axis to the frame valve section which contains attaching posts. For the bicuspid valve there are two posts, for the tricuspid valve there are three posts. The coupling formed this way enables coherence and ensures undisturbed work of the valve with full coaptation (apposition) of the leaflets which translates into a favourable hemodynamic profile of the prosthetic heart valve mentioned thereover.

A surgical suture with needles on both ends is used for creating a commissure. In the middle section of the suture between two ends a protrusion is made, favourably a knot, which is afterward located inside a pocket which is formed by pressing the edge of a material surplus in the place of vertical attachment of the valve frame in the valve section. The knot is located in the distance of 1-2 mm from the frame edge. By turns each suture is led with a needle through the edges of the formed pocket from the two opposite sides towards the valve frame. Each suture by turns goes through the inner part of the formed pocket. Then it is led from the outer part back into the inside of the pocket, afterwards it goes through the opposite edge. This manner of dragging is repeated severalfold for each of the sutures in order to approximate two edges tightly, thanks to which a commissure is formed and the valve leaflet is formed. Consecutively the other unattached suture ends on the valve frame are mounted by means of surgical knots to the attaching elements in the valve section of the valve frame.

The invention claimed is:

1. A biological low profile balloon expandable prosthetic heart valve,
    particularly aortic for transcatheter implantation comprising:
    a valve frame of cylindrical design which consists of a valve section, along with a supporting section; and
    a single continuous cylindrical biological material sewn to the valve frame wherein an upper part of the cylindrical biological material is folded into a cuff and is attached to the valve frame supporting section on an outside of the frame and the cuff is folded into the interior of the frame wherein the cuff is attached to posts in the valve section, and the upper parts of the cuff which are not attached to the posts, on each side of the post are connected with each other on the valve frame establishing commissures thereby forming valve leaflets.

2. The biological prosthetic aortic valve of claim 1 wherein the posts for attaching the cuff in the valve section is done by sewing, favorably by use of surgical suture.

3. The biological prosthetic aortic valve of claim 1 wherein the commissures in the frame area and in the area of the post for attaching the cuff are formed by sowing with a monofilament suture, whose both ends alternately conducted through the adjacent edges of the formed valve leaflets move towards the frame, and on the first suture line between the valve leaflets there is a protrusion made on the suture, favorably in the form of a knot.

4. A method of manufacturing a biological low profile balloon expandable prosthetic heart valve, particularly aortic for transcatheter implantation comprising: providing a valve frame of cylindrical design which consists of a valve section, a supporting section; and providing a single continuous biological material forming a cylindrical cuff from an upper part of the biological material;

attaching the material to the valve frame in the supporting section on the exterior of the valve frame;

folding the cuff to the interior of the frame;

attaching parts of the cuff to posts in the valve section, and forming commissures from upper parts of the cuff which are not attached to the posts, on each side of the post are connected with each other on the valve frame; and using the commissures for the valve leaflets.

5. The method of claim 4 forming the commissure in the frame area and in the area of the post for attaching the cuff is done with a monofilament suture, whose both ends alternately conducted through the adjacent edges of the formed valve leaflets move towards the frame on the distance of 2 mm, and on the first suture line between the valve leaflets there is a protrusion specifically made on the suture, favourably in the form of a knot.

\* \* \* \* \*